United States Patent
Stumbaugh et al.

(10) Patent No.: US 11,906,521 B2
(45) Date of Patent: *Feb. 20, 2024

(54) METHOD OF DETECTING AN ENDOTOXIN USING LIMULUS AMEBOCYTE LYSATE SUBSTANTIALLY FREE OF COAGULOGEN

(71) Applicant: LONZA WALKERSVILLE, INC., Walkersville, MD (US)

(72) Inventors: Candice Stumbaugh, Chambersburg, PA (US); David S. Herbst, Frederick, MD (US); Kenneth E. Nichols, Jr., Falling Waters, WV (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 127 days.

This patent is subject to a terminal disclaimer.

(21) Appl. No.: 17/482,918

(22) Filed: Sep. 23, 2021

(65) Prior Publication Data
US 2022/0074940 A1  Mar. 10, 2022

Related U.S. Application Data

(62) Division of application No. 15/668,101, filed on Aug. 3, 2017, now Pat. No. 11,156,614.

(60) Provisional application No. 62/370,493, filed on Aug. 3, 2016.

(51) Int. Cl.
*G01N 33/579* (2006.01)
*C12Q 1/37* (2006.01)

(52) U.S. Cl.
CPC ............ *G01N 33/579* (2013.01); *C12Q 1/37* (2013.01); *C12Q 2337/12* (2013.01); *G01N 2400/50* (2013.01)

(58) Field of Classification Search
None
See application file for complete search history.

(56) References Cited

U.S. PATENT DOCUMENTS

| | | | |
|---|---|---|---|
| 4,322,217 A | 3/1982 | Dikeman | |
| 5,208,148 A | 5/1993 | Haugland et al. | |
| 5,242,805 A | 9/1993 | Naleway et al. | |
| 5,310,657 A | 5/1994 | Berzofsky | |
| 5,362,628 A | 11/1994 | Haugland et al. | |
| 5,576,424 A | 11/1996 | Mao et al. | |
| 5,695,948 A | 12/1997 | Tanaka et al. | |
| 5,773,236 A | 6/1998 | Diwu et al. | |
| 5,830,912 A | 11/1998 | Gee et al. | |
| 7,846,678 B2 | 12/2010 | Pepe et al. | |
| 11,352,656 B2 * | 6/2022 | Stumbaugh | G01N 33/579 |
| 2010/0203071 A1 | 8/2010 | Blais et al. | |
| 2018/0208964 A1 | 7/2018 | Stumbaugh et al. | |
| 2022/0267824 A1 * | 8/2022 | Stumbaugh | C12Q 1/37 |

FOREIGN PATENT DOCUMENTS

| | | |
|---|---|---|
| CN | 102305788 A | 1/2012 |
| CN | 104155442 A | 11/2014 |
| EP | 0507952 A1 | 10/1992 |
| EP | 0426395 B1 * | 1/1997 |
| EP | 0426395 B1 | 1/1997 |
| JP | 2014-014375 A | 1/2014 |
| WO | 2012/057609 A1 | 5/2012 |
| WO | 2018/026941 A1 | 2/2018 |
| WO | 2018/132562 A1 | 7/2018 |
| WO | 2019/006000 A1 | 1/2019 |

OTHER PUBLICATIONS

Chromogenix, S-2423 Data Sheet, created on Nov. 6, 1997, retrieved online at http://www.chromogenicsubstrates.com/downloads/chromogenic_substrates_s2423.pdf.

Du Moulin et al., "Detection of Gram-Negative Bacteremia by Limulus Amebocyte Lysate Assay: Evaluation in a Rat Model of Peritonitis," J Infect Dis 151(1):148-152 (1985).

Harada-Suzuki et al., Further Studies on the Chromogenic Substrate Assay Method for Bacterial Endotoxins Using Horseshoe Crab (*Tachypleus tridentatus*) Hemocyte Lysate, J Biochem 92:793-800 (1982).

Hurley, "Endotoxemia: Methods of detection and clinical correlates," Clinical Microbiology Reviews 8(2):268-292 (1995).

"LAL Reagent Products for Detection of Bacterial Endotoxin; PYROSTAR™, " Wako Chemicals, pp. 1-14 (2014). Downloaded from <https://5.imimg.com/data5/AY/HF/MY-819970/bacterial-endotoxin-test-kit.pdf>.

Lindasay et al., "Single-Step, Chromogenic Limulus Amebocyte Lysate Assay for Endotoxin," Journal of Clinical Microbiology 27(5):947-951 (1989).

Miyata et al., "The Amino Acid Sequence of Coagulogen Isolated from Southeast Asian Horseshoe Crab, *Tachypleus gigas*," J. Biochem. 95(6):1793-1801 (1984).

Nachum et al., "Chromogenic Limulus Amebocyte Lysate Assay for Rapid Detection of Gram-Negative Bacteriuria," J. Clin. Microbiol. 21(5):759-763 (1985).

(Continued)

*Primary Examiner* — Sudhakar Katakam
*Assistant Examiner* — Zachary J Miknis
(74) *Attorney, Agent, or Firm* — MEDLER FERRO WOODHOUSE & MILLS PLLC

(57) ABSTRACT

The present invention is related to a method of detecting an endotoxin in a sample using a chromogenic assay, the method comprising: (a) contacting the sample with a reagent comprising limulus amebocyte lysate (LAL) and a chromogenic substrate; and (b) measuring a chromogenic effect resulting from a change in the chromogenic substrate in the presence of endotoxin in the sample; wherein the LAL is substantially free of coagulogen. The method also relates to compositions and kits comprising LAL substantially free of coagulogen, and methods of making such.

11 Claims, 11 Drawing Sheets

Specification includes a Sequence Listing.

(56) References Cited

OTHER PUBLICATIONS

Nakamura et al., "Fractionation of Limulus amebocyte lysate—Characterization of activation of the proclotting enzyme by an endotoxin-mediated activator," Biochimica et Biophysica Acta 707(2):217-225 (1982).

Novitsky, "Limulus amebocyte lysate (LAL) detection of endotoxin in human blood," Journal of Endotoxin Research 1(4): 253-263 (1994).

Obayashi et al., "A new chromogenic endotoxin-specific assay using recombined limulus coagulation enzymes and its clinical applications," Clinica Chimica Acta 149:55-65 (1985).

"Pyrochrome for the Detection and Quantification of Gram Negative Bacterial Endotoxins (Lipopolysaccharides)," Associates of Cape Cod Incorporated, Jan. 2011. Downloaded from ttps://www.acciusa.com/pdfs/accProduct/Pyrochrome_multilang_IFUs/PyrochromeIFU_PN000856_en_r3.pdf.

"PyroGene Recombinant Factor C Endotoxin Detection Assay," Product Insert, Lonza Pharma & Biotech (2012).

Srimal et al., "The Complete Amino Acid Sequence of Coagulogen Isolated from Southeast Asian Horseshoe Crab, *Carcinoscorpius rotundicauda*," J. Biochem. 98(2):305-318 (1985).

Torano et al., "Properties of the Clotting Enzyme Responsible for Endotoxin-Mediated Limulus Coagulation," Thrombosis Research 34(5):407-417 (1984).

International Search Report and Written Opinion for PCT/US2017/045137, dated Jan. 17, 2018.

International Search Report issued in international application No. PCT/US2018/013310, dated Mar. 28, 2018.

Non-final Office Action issued in U.S. Appl. No. 15/868,318, dated Sep. 11, 2019.

Final Office Action issued in U.S. Appl. No. 15/868,318, dated Jan. 13, 2020.

Advisory Action issued in U.S. Appl. No. 15/868,318, dated Mar. 30, 2020.

Advisory Action issued in U.S. Appl. No. 15/868,318, dated Apr. 23, 2020.

Non-final Office Action issued in U.S. Appl. No. 15/868,318, dated Oct. 8, 2020.

Final Office Action issued in U.S. Appl. No. 15/868,318, dated Jan. 15, 2021.

Non-final Office Action issued in U.S. Appl. No. 15/868,318, dated Mar. 20, 2021.

Final Office Action issued in U.S. Appl. No. 15/868,318, dated Jul. 20, 2021.

Advisory Action issued in U.S. Appl. No. 15/868,318, dated Sep. 24, 2021.

Brawner et al., "Heat pretreatment eliminates spurious butyrylcholinesterase enhancement of endotoxin levels in the kinetic chromogenic assay," Chemico-Biological Interactions 249:19-22 (2016).

Corrected Notice of Allowance issued in U.S. Appl. No. 15/868,318, dated Apr. 27, 2022.

Notice of Allowance issued in U.S. Appl. No. 15/868,318, dated Feb. 9, 2022.

Corrected Notice of Allowability issued in U.S. Appl. No. 15/868,318, dated Mar. 1, 2022.

Anonymous, "What is a Kilodalton (KD)?"; Aisimo Corp., downloaded from http://www.aisimo.com/faq/membrane-filter/85.php on Jan. 21, 2022. (Year: 2009).

Non-Final Office Action issued in U.S. Appl. No. 17/737,578, dated Jun. 1, 2023.

\* cited by examiner

| Endo. Stds. | 200mOD | | 100mOD | | 50mOD | |
|---|---|---|---|---|---|---|
| | Lystate Rxn. Time | Lystate-Coag. Rxn. Time | Lystate Rxn. Time | Lystate-Coag. Rxn. Time | Lystate Rxn. Time | Lystate-Coag. Rxn. Time |
| 0 EU/ml | 2557 | 2847 | 2272 | 2318 | 2010 | 1915 |
| 0.001 EU/ml* | 2644 | 2710 | 2295 | 2231 | 2044 | 1811 |
| 0.005 EU/ml | 2552 | 2429 | 2198 | 1962 | 1943 | 1547 |
| 0.05 EU/ml | 1972 | 1524 | 1743 | 1201 | 1525 | 943 |
| 0.5 EU/ml | 1018 | 781 | 900 | 622 | 779 | 496 |
| 5 EU/ml | 544 | 425 | 473 | 324 | 406 | 249 |
| 50 EU/ml | 276 | 195 | 205 | **** | 169 | **** |
| Corr. Coeff. | -0.991 | -0.998 | -0.985 | -0.998 | -0.984 | -0.997 |
| Slope | -0.249 | -0.275 | -0.263 | -0.263 | -0.270 | -0.266 |
| Blank to 0.005EU/ml Separation (Secs.) | 5 | 418 | 74 | 356 | 67 | 368 |
| 0.005EU/ml Reaction Time (Mins.) | 43 | 40 | 37 | 33 | 32 | 26 |
| Blank to 0.001EU/ml Separation (Secs.) | -87 | 137 | -23 | 87 | -34 | 104 |
| 0.001EU/ml Reaction Time (Mins.) | 44 | 45 | 38 | 37 | 34 | 30 |

*0.001EU/ml reaction time not included in calculation of line

FIG. 2

Current lowest Std.

| | Formulation | 0EU/ml | 0.005EU/ml | 0.05EU/ml | 0.5EU/ml | 5EU/ml | 50EU/ml | Sepa. 0-0.005EU/ml |
|---|---|---|---|---|---|---|---|---|
| 1 | 20%L, 0.004%Z | 6301 | 4918 | 2559 | 1415 | 828 | 495 | 1383 |
| 2 | 20%L, 0.008%Z | 5322 | 3980 | 2030 | 1139 | 697 | 441 | 1342 |
| 3 | 20%L, 0.012%Z | 4895 | 3683 | 1872 | 1069 | 666 | 433 | 1212 |
| 4 | 20%L, 0.016%Z | 5151 | 3946 | 2016 | 1142 | 724 | 453 | 1205 |
| 5 | 20%L, 0.020%Z | 4428 | 3246 | 1723 | 997 | 631 | 423 | 1182 |
| 6 | 30%L, 0.004%Z | 4594 | 3788 | 2209 | 1220 | 677 | 373 | 806 |
| 7 | 30%L, 0.008%Z | 4522 | 3915 | 2163 | 1182 | 656 | 364 | 607 |
| 8 | 30%L, 0.012%Z | 3864 | 3473 | 2016 | 1104 | 639 | 362 | 391 |
| 9 | 30%L, 0.016%Z | 3981 | 3481 | 2008 | 1097 | 653 | 382 | 500 |
| 10 | 30%L, 0.020%Z | 3896 | 3379 | 1940 | 1057 | 626 | 385 | 517 |
| 11 | 40%L, 0.004%Z | 3716 | 3469 | 2275 | 1247 | 695 | 365 | 247 |
| 12 | 40%L, 0.008%Z | 3648 | 3616 | 2175 | 1201 | 682 | 357 | 32 |
| 13 | 40%L, 0.012%Z | 3405 | 3328 | 2129 | 1127 | 630 | 344 | 77 |
| 14 | 40%L, 0.016%Z | 3443 | 3310 | 1988 | 1086 | 621 | 352 | 133 |
| 15 | 40%L, 0.020%Z | 3401 | 3174 | 2029 | 1069 | 604 | 341 | 227 |
| 16 | 50%L, 0.004%Z | 3282 | 3154 | 2197 | 1177 | 627 | 314 | 128 |
| 17 | 50%L, 0.008%Z | 3238 | 3264 | 2120 | 1136 | 610 | 313 | -26 |
| 18 | 50%L, 0.012%Z | 3141 | 2993 | 2098 | 1084 | 595 | 308 | 148 |
| 19 | 50%L, 0.016%Z | 3058 | 2946 | 1981 | 1047 | 585 | 305 | 112 |
| 20 | 50%L, 0.020%Z | 3064 | 2973 | 2027 | 1053 | 582 | 306 | 91 |
| 21 | CONT 22%L, 0.004%Z | 4432 | 3718 | 2035 | 1129 | 691 | 429 | 714 |

Lowest Std. <3600sec | Separation >200sec

FIG.3

|  | Formulation | 0EU/ml | 0.005EU/ml | 0.05EU/ml | 0.5EU/ml | 5EU/ml | 50EU/ml | Sepa. 0~0.005EU/ml |
|---|---|---|---|---|---|---|---|---|
| 1 | 20%L-co., 0.004%Z | 8147 | 6176 | 2959 | 1463 | 818 | 430 | 1971 |
| 2 | 20%L-co., 0.008%Z | 7781 | 5901 | 2693 | 1346 | 762 | 396 | 1880 |
| 3 | 20%L-co., 0.012%Z | 7323 | 4878 | 2339 | 1191 | 668 | 365 | 2445 |
| 4 | 20%L-co., 0.016%Z | 7252 | 4938 | 2215 | 1132 | 642 | 360 | 2314 |
| 5 | 20%L-co., 0.020%Z | 7070 | 4698 | 2129 | 1076 | 613 | 341 | 2372 |
| 6 | 30%L-co., 0.004%Z | 5709 | 4767 | 2633 | 1340 | 823 | 478 | 942 |
| 7 | 30%L-co., 0.008%Z | 6273 | 4889 | 2341 | 1245 | 766 | 455 | 1384 |
| 8 | 30%L-co., 0.012%Z | 5630 | 4126 | 2081 | 1116 | 693 | 408 | 1504 |
| 9 | 30%L-co., 0.016%Z | 5207 | 3792 | 1982 | 1054 | 654 | 376 | 1415 |
| 10 | 30%L-co., 0.020%Z | 5152 | 3662 | 1854 | 1002 | 607 | 366 | 1490 |
| 11 | 40%L-co., 0.004%Z | 5094 | 4211 | 2504 | 1302 | 783 | 412 | 883 |
| 12 | 40%L-co., 0.008%Z | 4762 | 4222 | 2410 | 1231 | 741 | 404 | 540 |
| 13 | 40%L-co., 0.012%Z | 4572 | 3698 | 1960 | 1033 | 631 | 353 | 874 |
| 14 | 40%L-co., 0.016%Z | 4517 | 3515 | 1879 | 1001 | 625 | 331 | 1002 |
| 15 | 40%L-co., 0.020%Z | 4355 | 3350 | 1683 | 906 | 556 | 315 | 1005 |
| 16 | 50%L-co., 0.004%Z | 4090 | 3348 | 2233 | 1126 | 681 | 335 | 742 |
| 17 | 50%L-co., 0.008%Z | 3956 | 3451 | 2051 | 1038 | 632 | 318 | 505 |
| 18 | 50%L-co., 0.012%Z | 3734 | 3308 | 1811 | 948 | 585 | 293 | 426 |
| 19 | 50%L-co., 0.016%Z | 3629 | 3003 | 1659 | 880 | 569 | 290 | 626 |
| 20 | 50%L-co., 0.020%Z | 3644 | 2881 | 1550 | 816 | 494 | 272 | 763 |
| 21 | CONT 22%L, 0.004%Z | 4432 | 3718 | 2035 | 1129 | 691 | 429 | 714 |

Lowest Std. <3600sec / Separation >200sec

Current lowest Std.

0.005EU/ml reacted in less than 1hr for with passing separation (rows 14–20)

FIG.4

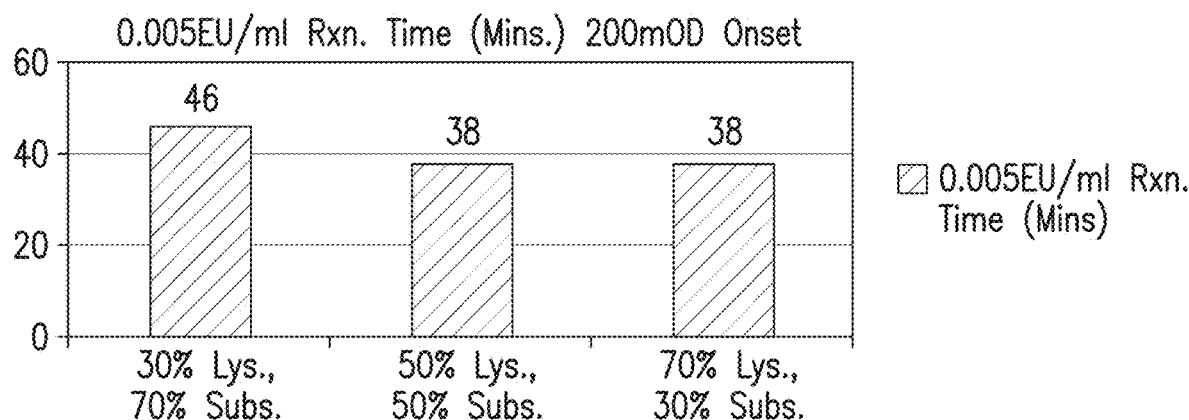
FIG.5A
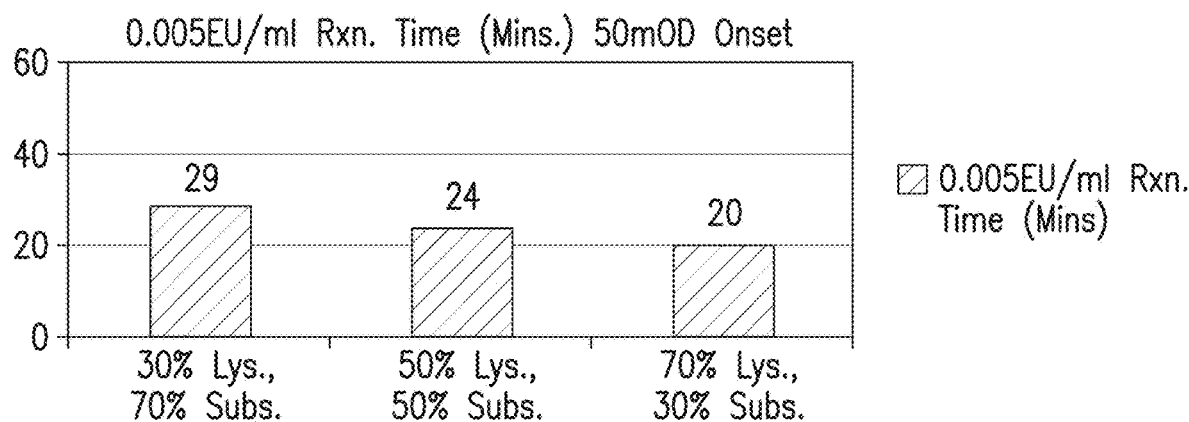
FIG.5B
|  | Current | New | Current | New |
|---|---|---|---|---|
| Sensitivity | 0.005EU/ml | 0.005EU/ml | 0.001 EU/ml | 0.001 EU/ml |
| Reaction Time | 60 mins | 20 mins | NA | 27 to 45 mins |
| Separation | ≤300 secs | Sufficient | NA | Sufficient |
FIG.5C

| Lot | 0.005EU/ml Rxn. (mins.) | 0.001EU/ml Rxn. (mins.) |
|---|---|---|
| 1 | 20 | 21 |
| 2 | 24 | 31 |
| 3 | 17 | 20 |

FIG.6A

METHOD OF DETECTING AN ENDOTOXIN USING LIMULUS AMEBOCYTE LYSATE SUBSTANTIALLY FREE OF COAGULOGEN

SEQUENCE LISTING

The instant application contains a Sequence Listing which has been submitted electronically in ASCII format and is hereby incorporated by reference in its entirety. Said ASCII copy, created on Sep. 5, 2017, is named 0132-0023WO1_SL.txt and is 1,055 bytes in size.

FIELD OF THE INVENTION

The present invention is related to a method of detecting an endotoxin in a sample using a chromogenic assay, the method comprising: (a) contacting the sample with a reagent comprising limulus amebocyte lysate (LAL) and a chromogenic substrate; and (b) measuring a chromogenic effect resulting from a change in the chromogenic substrate in the presence of endotoxin in the sample, wherein the LAL is substantially free of coagulogen. The method also relates to compositions and kits comprising LAL substantially free of coagulogen, and methods of making such.

BACKGROUND OF THE INVENTION

Gram negative bacterial endotoxin is a biological pyrogen that causes fever when introduced intravenously. The endotoxin, also known as lipopolysaccharide (LPS), is found in the outer membrane of Gram-negative bacteria, such as *Salmonella, Escherichia coli, Shigella* and *Neisseira*. The toxicity mechanism that the endotoxins trigger is caused by the lipid fraction of the lipopolysaccharides. For example, when the lysis of the bacteria within an organism takes place, the response in the presence of the lipids that go into the bloodstream can be through the activation of the complement system. This lipid fraction leads to the release of different cytokines, such as interleukins 1 and 8. The production of the tumour necrosis factor may also be activated. The infection produced is associated with inflammatory processes and can pose a great danger for the infected organism. Interleukins 1 are a series of cytokines that the organism releases as an immune response and against the inflammation. This signal leads to the migration of neutrophils towards the place where the infection has occurred, producing chemotaxis. This facilitates the occurrence of phagocytosis; however, in some cases, depending on the state of the immune system of the individual and the level of infection, the endotoxin could lead to generalized sepsis, along with the risks that are brought about by the sepsis. It is known that there are many cases where the Gram-negative bacteria have caused multiple organ failure and even death by systemic infection in higher mammals. Due to the adverse effects associated with endotoxins, it is critical for the pharmaceutical industry and healthcare community to have an early and sensitive detection of endotoxin.

The Limulus Amebocyte Lysate (LAL) test was commercially introduced in the 1970s as a way to detect endotoxins. LAL is derived from the blood cells, or amebocytes, of the horseshoe crab, *Limulus polyphemus*. The original LAL test constituted a cascade of serine proteases which are triggered by trace levels of endotoxin, culminating in a gel clot at the end of the reaction. Factor C, which normally exists as a zymogen, is the primer of this coagulation cascade. In vivo, Factor C is the perfect biosensor, which alerts the horseshoe crab of the presence of a Gram-negative invader. The hemostatic end-point entraps the invader, killing it and limiting further infection.

The LAL test can be modified to use different methods to measure the response of the amebocytes against the endotoxins. These methods include the so-called Gel-Clot method, turbidimetric and chromogenic methods. These LAL tests are recommended in international pharmacopoeias as the method for detecting bacterial toxins both in the raw materials used for the production of medicines and for the final products. These tests are also useful for the cosmetics industry and in food production as it is the method recommended by the FDA (Food and Drug Administration) for the detection of pyrogens.

BRIEF SUMMARY OF THE INVENTION

Provided herein are methods of detecting an endotoxin in a sample using a chromogenic assay comprising a limulus amebocyte lysate (LAL) substantially free of coagulogen.

Embodiments herein are directed to a method of detecting an endotoxin in a sample using a chromogenic assay, the method comprising: (a) contacting the sample with a reagent comprising limulus amebocyte lysate (LAL) and a chromogenic substrate; and (b) measuring a chromogenic effect resulting from a change in the chromogenic substrate in the presence of endotoxin in the sample, wherein the LAL is substantially free of coagulogen.

In some embodiments, the chromogenic substrate is a p-nitroaniline covalently bonded to a greater than three amino acids. In some embodiments, the chromogenic substrate is Ac-Ile-Glu-Ala-Arg-pNA (SEQ ID NO: 1). In some embodiments, the change in the chromogenic substrate occurs due to an enzymatic reaction. In some embodiments, the enzymatic reaction is cleavage of a chromophore from a polypeptide. In some embodiments, the chromogenic effect is measured by detecting at absorbance at 380 nm-420 nm. In some embodiments, chromogenic effect is measured by detecting absorbance at 405 nm.

In some embodiments, the reagent is a liquid. In some embodiments, the reagent is an aqueous liquid. In some embodiments, the reagent is lyophilized and then reconstituted in an aqueous liquid prior to contacting with the sample.

In some embodiments, the LAL is lyophilized, and then reconstituted prior to contacting with the sample. In some embodiments, the chromogenic substrate is lyophilized, and then reconstituted prior to contacting with the sample.

In some embodiments, the sample is a biological sample. In some embodiments, the sample is selected from the group consisting of a parenteral dosage form, vaccine, antibiotic, therapeutic protein, therapeutic nucleic acid, therapeutic antibody, and biological product. In some embodiments, the LAL substantially free of coagulogen has less than 5% (wt/wt) of coagulogen relative to total protein in the LAL as measured by SDS-PAGE and confirmed by Western blot. In some embodiments, the LAL substantially free of coagulogen has less than 2% (wt/wt) of coagulogen relative to total protein in the LAL. In some embodiments, the LAL substantially free of coagulogen has less than 0.5% (wt/wt) of coagulogen relative to total protein in the LAL. In some embodiments, the chromogenic assay is conducted using single cuvette spectroscopy, multiple cuvette spectroscopy, or a microplate reader.

In some embodiments, the method further comprises comparing the chromogenic effect to a standard to determine the quantity of endotoxin in the sample.

In some embodiments, the disclosure is directed to a method of detecting an endotoxin in a biological sample using a chromogenic assay, the method comprising: (a) contacting the biological sample with an aqueous reagent comprising limulus amebocyte lysate (LAL) and Ac-Ile-Glu-Ala-Arg-pNA (SEQ ID NO: 1); (b) measuring the change in absorbance at 405 nm resulting from the enzymatic cleavage of pNA from Ac-Ile-Glu-Ala-Arg-pNA (SEQ ID NO: 1) in the presence of endotoxin in the sample; wherein the LAL is substantially free of coagulogen.

In some embodiments, the method of the present disclosure has increased sensitivity. In some embodiments, the method has a sensitivity of >0.001 EU/mL endotoxin.

In some embodiments, the method of the present disclosure is directed to a composition comprising limulus amebocyte lysate (LAL) and a chromogenic substrate, wherein the LAL is substantially free of coagulogen. In some embodiments, the chromogenic substrate is Ac-Ile-Glu-Ala-Arg-pNA (SEQ ID NO: 1). In some embodiments, the LAL and chromogenic substrate are lyophilized. In some embodiments, the LAL and chromogenic substrate are in an aqueous solution.

In some embodiments, the method of the present disclosure is directed to a kit comprising: (a) limulus amebocyte lysate (LAL), wherein the LAL is substantially free of coagulogen; (b) a chromogenic substrate; and (c) instructions for detecting an endotoxin using the LAL and chromogenic substrate.

In some embodiments, the LAL is lyophilized. In some embodiments, the LAL is in an aqueous solution. In some embodiments, the LAL and the chromogenic substrate are in a single container. In some embodiments, the kit further comprises a sterile container comprising the LAL. In some embodiments, the sterile container is a sterile vial. In some embodiments, the kit further comprises a control standard endotoxin.

In some embodiments, the disclosure is directed to a method of making limulus amebocyte lysate (LAL) substantially free of coagulogen, the method comprising: (a) providing a composition comprising LAL, wherein the LAL comprises coagulogen; (b) adjusting the buffer; and (c) subjecting the composition of (b) to tangential flow filtration using a 20 kDa to 50 kDa filter, thereby isolating LAL substantially free of coagulogen.

In some embodiments, the TFF is performed at a flow rate of 350 ml/min to 500 ml/min. In some embodiments, the buffer is a Tris buffer or MES buffer. In some embodiments, the buffer has a pH of about 7.0 to 8.0. In some embodiments, the filter is tangential flow filtration (TFF). In some embodiments, the TFF filter is a modified polyethersulfone (mPES) membrane filter.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology.

FIG. 2: Comparison of samples comprising regular LAL versus LAL substantially free of coagulogen shows an increase in separation at multiple onset milli optical density (mOD) values. EU/ml=endotoxin units per milliliter.

FIG. 3: Comparison of the effect of the concentration of standard LAL (L) and zwittergent (Z) on the speed of reaction. Increasing the concentration of L and Z increases the speed of the reaction of each standard. Separation is lost between the blank and lowest standard (0.005 EU/ml) as the speed of the reaction increases.

FIG. 4: Comparison of the effect of the concentration of LAL substantially free of coagulogen (L-co) and zwittergent (Z) on the speed of reaction. Increasing the concentration of L-co and Z increases the speed of the reaction of each standard. Separation of at least 200 seconds is maintained for all formulations. L-co formulated with increased zwittergent achieved sensitivity of 0.001 EU/ml with acceptable separation (data not shown).

FIG. 5A: Reaction time of various concentrations for L-co and chromogenic substrate at 200 mOD. FIG. 5B: Reaction time of various concentrations for L-co and chromogenic substrate at 50 mOD. FIG. 5C summarizes the increased sensitivity, reaction time, and separation of assays using L-co relative to assays using L.

FIG. 6A: Reaction time of three separate lots of L-co, using 70% L-co preparation and 30% chromogenic substrate at 50 mOD (separation range: 732 seconds to 211 seconds).

DETAILED DESCRIPTION OF THE INVENTION

Figure 1:
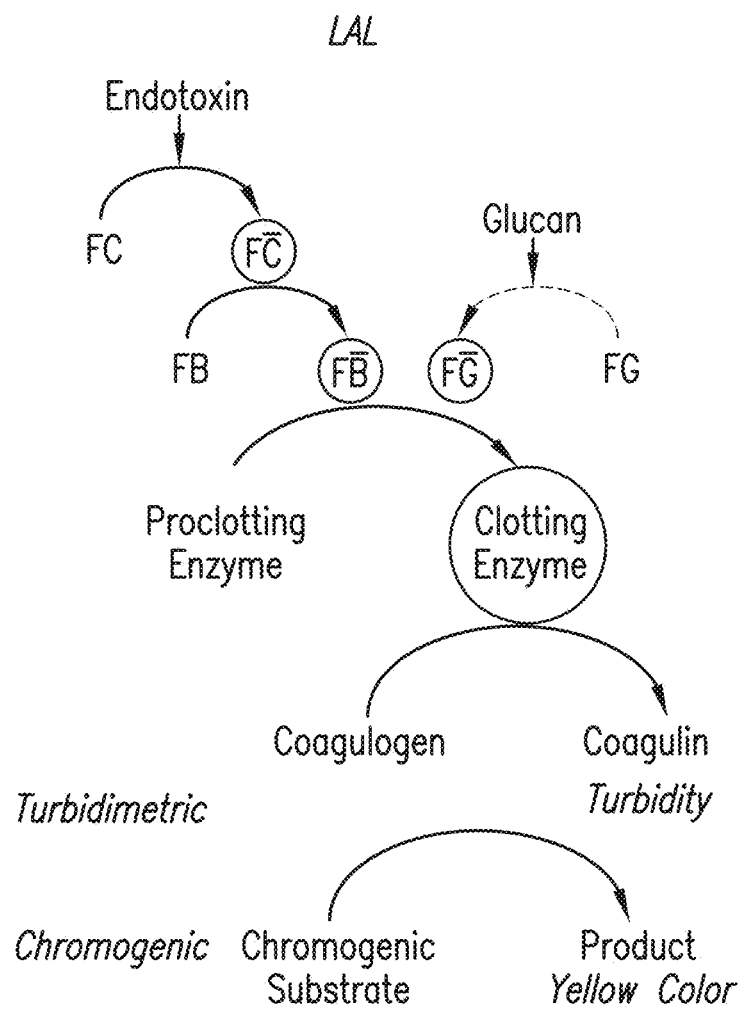
FIG. 1: Schematic representation of the endotoxin-associated cascade, including turbidity and chromogenic analytical points.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of skill in the art. The disclosures of any documents cited herein is incorporated by reference herein in their entireties.

In some embodiments, the invention is directed to methods of detecting an endotoxin. The term "endotoxin" generally refers to the lipopolysaccharide complex associated with the outer membrane of gram-negative bacteria. The term "endotoxin" is occasionally used to refer to any cell-associated bacterial toxin. While endotoxin refers to cell associated lipopolysaccharides, exotoxin refers to toxins secreted by bacteria and are predominantly polypeptides in nature.

The biological activity of endotoxin is associated with the lipopolysaccharide (LPS). Lipopolysaccharides are part of the outer membrane of the cell wall of gram-negative bacteria. Lipopolysaccharides are invariably associated with gram-negative bacteria whether the organisms are pathogenic or not. Toxicity is associated with the lipid component (Lipid A) and immunogenicity is associated with the polysaccharide components. The cell wall antigens (O antigens) of gram-negative bacteria are the polysaccharide components of LPS. In addition, LPS can elicit a variety of inflammatory responses in an animal.

Gram-negative bacteria, within animals, can release minute amounts of endotoxin while growing. This may result in the stimulation of natural immunity. It is known that small amounts of endotoxin may be released in a soluble form by young cultures grown in the laboratory. But for the most part, endotoxins remain associated with the cell wall until disintegration of the organisms. Disintegration of the bacterial organisms can result from autolysis, external lysis mediated by complement and lysozyme, and phagocytic digestion of bacterial cells. Bacterial endotoxin is abundant in the human gut. Elevated concentrations of endotoxins are associated with a number of conditions including some metabolic syndrome diseases. Metabolic syndrome diseases include, for example, atherosclerosis, insulin resistance, diabetes mellitus, and obesity. Increased endotoxin levels have also been associated with fatty liver disease and Crohn's disease. Endotoxin may also leak out of the GI tract when present at elevated levels. Endotoxin is a potent inflammatory antigen and leaking of the endotoxin can result in systemic inflammatory response.

Compared to the classic exotoxins of bacteria, endotoxins are less potent and less specific in their action, since they do not act enzymatically. Endotoxins are heat stable (boiling for 30 minutes does not destabilize endotoxin), but certain powerful oxidizing agents such as superoxide, peroxide and hypochlorite, have been reported to neutralize them. Since these are powerful oxidizing agents they are not particularly amenable to a therapeutic composition for neutralizing endotoxins.

The endotoxins of the present invention can originate from Gram-negative bacteria. Exemplary Gram-negative bacteria include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Corynebacteria* spp., *Citrobacter* spp., *Chlamydia* spp., *Brucella* spp., *Pseudomonas* spp., *Helicobacter* spp. and *Vibrio* spp. Gram negative bacteria also may be those that fall in the Enterobacteriaceae, Pseudomonadaceae, Neisseriaceae, Veillonellaceae, Bacteroidaceae, Vibrionaceae, Pasteurellaceae, and Fusobacteriaceae families. In some embodiments, the endotoxin is from *Salmonella* or *Escherichia* spp.

As used herein, the term "endotoxin activity" refers to portions of Gram-negative bacteria that can cause toxicity, including pyrogenicity and septic shock. The toxic effects attributed to endotoxin have been found to be associated with the glycosylated lipid A portion of a lipopolysaccharide molecule present in or derived from the outer membrane of Gram-negative bacteria.

The term "Lipopolysaccharide" (LPS) refers to large molecules consisting of a lipid and a polysaccharide (glycophospholipid) joined by a covalent bond. LPS comprises three parts: 1) 0 antigen; 2) Core oligosaccharide, and 3) Lipid A. The 0-antigen is a repetitive glycan polymer attached to the core oligosaccharide, and comprises the outermost domain of the LPS molecule. Core oligosaccharide attaches directly to lipid A and commonly contains sugars such as heptose and 3-deoxy-D-mannooctulosonic acid (also known as KDO, keto-deoxyoctulosonate). Lipid A is a phosphorylated glucosamine disaccharide linked to multiple fatty acids. The fatty acids anchor the LPS into the bacterial membrane, and the rest of the LPS projects from the cell surface. Bacterial death may result if LPS is mutated or removed.

Endotoxin activity resides in the lipid A domain portion of LPS. When bacterial cells are lysed by the immune system, fragments of membrane containing lipid A are released into the circulation, causing fever (pyrogenicity), diarrhea, and a potentially fatal shock (called endotoxic or septic shock). Toxicity of LPS is expressed by lipid A through the interaction with B-cells and macrophages of the mammalian immune system, a process leading to the secretion of proinflammatory cytokines, mainly tumor necrosis factor (TNF), which may have fatal consequences for the host. Lipid A also activates human T-lymphocytes (Th-1) "in vitro" as well as murine CD4+ and CD8+ T-cells "in vivo", a property which allows the host's immune system to mount a specific, anamnestic IgG antibody response to the variable-size carbohydrate chain of LPS. On these bases, LPS has been recently recognized as a T-cell dependent antigen "in vivo". Thus, in some embodiments, the method of the present invention is directed to detecting Lipid A.

In some embodiments, the endotoxin is detected using a chromogenic assay. As used herein, chromogenic assays measure or detects a change in absorbance in a chromogenic substrate (i.e., a chromogen) in the presence of an endotoxin. In some embodiments, the change in absorbance in the chromogenic substrate is due to enzyme activity. In some embodiments, the term "chromogenic substrate" refers to a substrate before and after enzymatic activity. For example, if the chromogenic substrate is a peptide-chromophore which is cleaved by an enzyme to result in a peptide and a chromophore, the term "chromogenic substrate" would refer to the peptide-chromophore, the cleaved peptide, and the release chromophore. In some embodiments, synthetic chromogens can be used. In some embodiments, a naturally produced chromogen can be used. In some embodiments, the chromogenic substrate is a synthetic peptide. In some embodiments, the substrates are very sensitive, i.e. they can detect very low enzyme activities.

The ability of a reagent comprising a chromogenic substrate to detect low enzyme concentrations makes them useful in, for example, the search for the presence of certain enzyme activities associated with endotoxins, either in research or in quality control procedures. Sometimes there is a lack of correspondence between a natural (i.e., natural substrate for the enzyme) and a synthetic chromogenic substrate in their responses to a certain enzyme preparation. In some embodiments, a chromogenic substrate is less selective, i.e. it has less discrimination in its reactivity towards related enzymes compared to the natural substrate.

The term "chromogenic substrate" refers to the substrate, e.g., compound or polypeptide, in the assay that changes its absorbance spectra, e.g., a change in color, in the presence of the endotoxin. Chromogenic substrate refers to substrates that both (i) absorb, and/or (ii) do not absorb at a specified wavelength. Thus, e.g., according to the present disclosure, a chromogenic substrate may originally not absorb at a specified wavelengths, (e.g., non-absorbing at visual wavelengths), and then in the presence of an endotoxin, may begin to absorb at the specified wavelengths (e.g., at visual wavelengths). Alternatively, e.g., a chromogenic substrate may originally absorb at a specified wavelength (e.g., absorb at visual wavelengths), and then in the presence of an endotoxin, may not absorb at the specified wavelength (e.g., not absorb at visual wavelengths). In some embodiments, the chromogenic substrate may absorb at a given wavelength in the absence of an endotoxin, and then absorb at a different wavelength in the presence of an endotoxin. The change in absorbance characteristics, i.e., chromogenic effect, at one or more specified wavelengths can be correlated with the presence of endotoxin.

In some embodiments, the chromogenic substrate is a chromogenic peptide substrate. In some embodiments, the chromogenic peptide substrate is initially colorless. In some embodiments, the chromogenic peptide substrate initially has a color, e.g., a color in the visual spectrum (approximately 390-700 nm). In some embodiments, when the chromogenic peptide substrate is cleaved by an enzyme, a color change can occur, e.g., a chromophore is release, causing a color change in the resulting product. In some embodiments, cleavage changes the optical properties of the product, which are different from those of the uncleaved substrate and which can be measured by means of spectrophotometry. Non-limiting examples of chromogenic groups which can be coupled to a peptide substrate are para-nitroaniline (pNA), 5-amino-2-nitrobenzoic acid (ANBA), 7-amino-4-methoxycoumarin (ANC), quinonylamide (QUA), dimethyl 5-aminoisophthalate (DPA) and their derivatives. Fluorogenic substrates include, without limitation, Z-Gly-Pro-Arg-AMC [Z=Benzyloxycarbonyl; AMC=7-amino-4-methylcoumarin], homovanillic acid, 4-hydroxy-3-methoxyphenylacetic acid, reduced phenoxazines, reduced benzothiazines, Amplex®, resorufin β-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236, incorporated by reference), 4-methylumbelliferyl β-D-galactopyranoside, carboxyumbelliferyl β-D-galactopyranoside and fluorinated coumarin β-D-galactopyranosides (U.S. Pat. No. 5,830,912, incorporated by reference).

A non-limiting chromogenic assay is an enzymatic activity assay based on the Factor C/Factor B cascade. Factor C, the first component in the cascade, is a protease zymogen that is activated by endotoxin binding. In some embodiments, the chromogenic assay uses a recombinant form of Factor C (rFC). In this pathway, Factor B is activated by Factor C. Factor B activates a pro-clotting enzyme into a clotting enzyme. In some embodiments, the pro-clotting enzyme effects a chromogenic change in a chromogenic substrate. In some embodiments, the chromogenic assay is an LAL assay, e.g., the Endpoint Chromogenic LAL Assays from Lonza.

In some embodiments, the chromogenic assay is an LAL assay, wherein the initial part of the LAL endotoxin reaction activates a proclotting enzyme, which in turn enzymatically cleaves p-nitroaniline (pNA) from a synthetic substrate, producing a yellow color.

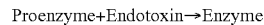

Proenzyme+Endotoxin→Enzyme

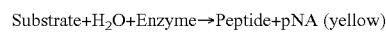

Substrate+H$_2$O+Enzyme→Peptide+pNA (yellow)

In some embodiments, gram-negative bacterial endotoxin can indirectly catalyze the activation of a proenzyme in the LAL. The initial rate of activation can be determined by the concentration of endotoxin present.

In some embodiments, the change in chromogenic substrate occurs due to an enzymatic reaction. In some embodiments, the enzymatic reaction results in cleavage of a peptide bond, thereby cleaving a chromophore substituent (e.g., p-NA) from a polypeptide. For example, the activated enzyme can catalyze the release of pNA from a colorless peptide substrate, e.g., Ac-Ile-Glu-Ala-Arg-pNA (SEQ ID NO: 1). In some embodiments, the peptide substrate is a p-nitroaniline covalently bonded to greater than three amino acids. In some embodiments, embodiments, the chromogenic substrate is Ac-Ile-Glu-Ala-Arg-pNA (SEQ ID NO: 1). In some embodiments, the chromogenic assay measures free pNA. In some embodiments, the chromogenic assay measures free pNA photometrically at an absorbance of 380 nm to 410 nm, e.g., 400 nm to 410 nm, or 405 nm. Methods of measuring absorbance are well known to those in the art. In some embodiments, the chromogenic assay is conducted using single cuvette spectroscopy, multiple cuvette spectroscopy, or a microplate reader to measure absorbance.

The free pNA can be measured photometrically at 380 nm to 410 nm, e.g., 405 nm, after the reaction is stopped with stop reagent. The concentration of endotoxin in a sample is calculated from a standard curve of absorbance values of solutions containing known amounts of an endotoxin standard.

One standard chromogenic assay for detecting endotoxin comprises contacting a sample with a reagent, wherein the reagent comprises limulus amebocyte lysate (LAL). In some embodiments, the reagent is a liquid, e.g., and aqueous liquid. Alternatively, the reagent can be lyophilized, and then reconstituted in an aqueous liquid, e.g., sterile water or buffer solution, prior to being contacted with the sample. In some embodiments, the reagent is a liquid. In some embodiments, the reagent is an aqueous liquid. In some embodiments, the reagent is lyophilized and then reconstituted in an aqueous liquid prior to contacting with the sample. In some embodiments, the LAL is lyophilized, and then reconstituted in the aqueous liquid prior to contacting with the sample. In some embodiments, the chromogenic substrate is lyophilized, and then reconstituted in an aqueous liquid prior to contacting with the sample. In some embodiments, lyophilization allows for a longer and/or more robust storage of the reagent, LAL, and or chromogenic substrate in the chromogenic assay. For example, in some embodiments, the lyophilized reagent, LAL and/or chromogenic substrate allows for greater than 20%, greater than 30%, greater than 40%, greater than 50%, greater than 60%, greater than 70%, greater than 80%, greater than 90% or greater than 100% increase in time of stability relative to a non-lyophilized reagent, LAL, and or chromogenic substrate in the chromogenic assay. "Stability" as used in this context refers to the assay functioning for its intended purpose, i.e., for detecting endotoxin at the same speed and sensitivity. For example, if a non-lyophilized reagent is stable for 3 weeks, a lyophilized reagent stable for 6 weeks would have a "100% increase" in time of stability.

The present disclosure provides for an improved method for detecting an endotoxin in a sample. The term "sample" can include any substance, compound, tool or instrument. However, for practical purposes, the sample can include a substance, compound, tool or instrument that has contact with a biological organism, e.g., a mammal, human, domesticated animal, or zoo animal. The term "sample" can refer to any medical device, pharmaceutical and biotech product in which sources of endotoxin (from raw material receipt through the end of the manufacturing process) may make the sample unsuitable for contact with cerebral spinal fluid or the cardiovascular system. In some embodiments, the term sample refers to a medical device which comes in contact with cerebral spinal fluid or cardiovascular system in vivo, e.g., with a human. In some embodiments, the term sample refers to a biological sample. In some embodiments, the sample is selected from the group consisting of a parenteral dosage form, vaccine, antibiotic, therapeutic protein, therapeutic nucleic acid, therapeutic antibody, and biological product.

The term "limulus amebocyte lysate" (LAL) refers to an aqueous extract of blood cells (amoebocytes) from the horseshoe crab, *Limulus polyphemus*. The aqueous extract of blood cells from horseshoe crabs comprise coagulogen, a gel-forming protein of hemolymph that hinders the spread of invaders by immobilizing them. See, e.g., Iwanaga S, et al., *J. Biochem.* 98:305-318 (1985) and Iwanaga S, et al., *J. Biochem.* 95 (6): 1793-1801 (1984).

The clotting cascade system of the horseshoe crab (*Limulus*) is involved in both haemostasis and host defense. The cascade results in the conversion of coagulogen, a soluble protein, into an insoluble coagulin gel. The clotting enzyme excises the fragment peptide C from coagulogen, giving rise to aggregation of the monomers.

The term "coagulogen" refers to the polypeptide chain as found in Iwanaga (1984) and Iwanaga (1985), which is a single 175-residue polypeptide chain, that is cleaved after Arg-18 and Arg-46 by a clotting enzyme contained in the hemocyte and activated by a bacterial endotoxin (lipopolysaccharide). Cleavage releases two chains of coagulin, A and B, linked by two disulfide bonds, together with the peptide C. Gel formation results from interlinking of coagulin molecules. Secondary structure prediction suggests the C peptide forms an alpha-helix, which is released during the proteolytic conversion of coagulogen to coagulin gel. The beta-sheet structure and 16 half-cystines found in the molecule appear to yield a compact protein stable to acid and heat.

While coagulogen is important for gel formation (e.g., clotting assay), the present disclosure has found that it is not essential in a chromogenic assay. The present disclosure has found that chromogenic assays comprising LAL substantially free of coagulogen achieved increased levels of speed, sensitivity, and separation relative to chromogenic assays comprising LAL with naturally occurring amounts of coagulogen. Thus, in some embodiments, the invention is directed to a chromogenic assay comprising LAL substantially free of coagulogen.

In some embodiments, the LAL is substantially free of coagulogen. One of skill in the art, upon reading the present disclosure, would appreciate that a reduction in various amounts of coagulogen will result in increasing levels of speed, sensitivity and/or separation in a chromogenic assay, e.g., an LAL assay. In some embodiments, the term "substantially free" refers to LAL having less than 50%, less than 40%, less than 30%, less than 20%, less than 10%, less than 5%, less than 2%, less than 1% or less than 0.5% (wt/wt) of coagulogen relative to total protein in the LAL as measured by SDS-PAGE with protein stain and confirmed by Western blot. In some embodiments, the term "substantially free" refers to LAL having less than 10% or less than 5% (wt/wt) of coagulogen relative to total protein in the LAL as measured by SDS-PAGE with protein stain and confirmed by Western blot.

In some embodiments, the term substantially free LAL of coagulogen refers to LAL in which at least 60%, at least 70%, at least 80%, at least 90%, at least 95%, at least 97%, at least 98%, at least 99% or at least 99.5% (wt/wt) of coagulogen is removed relative to the amount of coagulogen in LAL in which the coagulogen has not been removed.

In some embodiments, the chromogenic assay determines the presence or absence of endotoxin in a sample. In other embodiments, the chromogenic assay can quantify the amount of endotoxin in a sample. In some embodiments, the method further comprises comparing the chromogenic effect of the endotoxin in a sample to a known endotoxin standard to determine the quantity of endotoxin in the sample.

In some embodiments, the disclosure is directed to a method of detecting an endotoxin in a biological sample using a chromogenic assay, the method comprising: (a) contacting the biological sample with an aqueous reagent comprising limulus amebocyte lysate (LAL) and Ac-Ile-Glu-Ala-Arg-pNA (SEQ ID NO: 1); (b) measuring the change in absorbance at 405 nm resulting from the enzymatic cleavage of pNA from Ac-Ile-Glu-Ala-Arg-pNA (SEQ ID NO: 1) in the presence of endotoxin in the sample; wherein the LAL is substantially free of coagulogen.

By removing the coagulogen from the LAL, the chromogenic assay can have increased sensitivity. In some embodiments, the method of the present disclosure has increased sensitivity. In some embodiments, the method has a sensitivity of less than 0.05 EU/mL, less than 0.03 EU/mL, less than 0.01 EU/mL, less than 0.008 EU/mL, less than 0.006 EU/mL, less than 0.005 EU/mL, less than 0.004 EU/mL, less than 0.003 EU/mL, less than 0.002 EU/mL, or less than 0.001 EU/mL.

The disclosure additionally is directed to compositions comprising (1) LAL substantially free of coagulogen, and (2) a chromogenic substrate. In some embodiments, the chromogenic substrate in the composition comprises pNA. In some embodiments, the chromogenic substrate in the composition is Ac-Ile-Glu-Ala-Arg-pNA (SEQ ID NO: 1).

In some embodiments, the composition comprises 60% to 80% LAL substantially free of coagulogen preparation, and 20% to 40% chromogenic substrate (wt/wt). In some embodiments, the composition comprises about 6% to about 25% LAL substantially free of coagulogen. In some embodiments, the composition comprises 70% LAL substantially free of coagulogen preparation, and 30% chromogenic substrate (wt/wt). In some embodiments, the composition comprises 70% LAL substantially free of coagulogen preparation, and 30% Ac-Ile-Glu-Ala-Arg-pNA (SEQ ID NO: 1) (wt/wt). In some embodiments, the compositions as described herein are in a single container, e.g., a single vial. In some embodiments, the compositions described herein are lyophilized. For example, the disclosure specifically describes a lyophilized composition comprising 70% LAL substantially free of coagulogen preparation, and 30% Ac-Ile-Glu-Ala-Arg-pNA (SEQ ID NO: 1) (wt/wt).

In some embodiments, the present invention is directed to a chromogenic assay kit. The kit can include one or more of the components normally associated with a LAL chromogenic assay, including a reagent comprising LAL and a chromogenic substrate. In some embodiments, the method of the present disclosure is directed to a kit comprising: (a) limulus amebocyte lysate (LAL), wherein the LAL is substantially free of coagulogen; (b) a chromogenic substrate; and (c) instructions for detecting an endotoxin using the LAL and chromogenic substrate. In some embodiments, the kit comprises various reagents, each reagent having LAL with a different amount of coagulogen removed.

The kit can comprise one or more containers. In some embodiments, the LAL and the chromogenic substrate are in a single container. In some embodiments, the LAL and the chromogenic substrate are in two distinct containers. In some embodiments, the kit comprises a sterile container comprising the LAL. In some embodiments, the kit comprises a reconstitution buffer, which can reconstitute the LAL and/or the chromogenic substrate for use in the assay. In some embodiments, the sterile container is a sterile vial. In some embodiments, the kit further comprises a control standard endotoxin, which can be used as a positive endotoxin control, or can be used to quantitate the amount of endotoxin in a standard. In some embodiments, the kit comprises more than one control standard endotoxin, at one or more concentrations.

One of skill in the art can appreciate that different methods may be used to remove the coagulogen from the LAL. Each of these methods, may differ in efficiency, rate of purification, cost, and effort, but are within the knowledge of the skilled artisan. The present disclosure comprises an improved method of making LAL substantially free to coagulogen using tangential flow filtration. Tangential flow filtration (TFF) refers to cross-flow filtration wherein the majority of the feed flow travels tangentially across the surface of the filter, rather than into the filter. The disclosure has found that by using TFF, the retentate comprising the majority of LAL proteins (which can foul the filter) is substantially washed away during the filtration process, and coagulogen is filtered into the permeate. In some embodiments, the TFF is a continuous process, unlike batch-wise dead-end filtration.

In some embodiments, the disclosure is directed to a method of making LAL substantially free to coagulogen, then method comprising subjecting the LAL to TFF. In some embodiments, then LAL is placed in a buffer prior to TFF. In some embodiments, the buffer is a Tris buffer or MES buffer. In some embodiments, the buffer has a pH of about 6.0 to about 9.0, or about 7.0 to about 8.0.

Various membranes can be used in the TFF. In some embodiments, the membrane is a 10 to 80 kDa filter, or a 20 to 50 kDa filter. Thus, in some embodiments, the disclosure is directed to a method of making limulus amebocyte lysate (LAL) substantially free of coagulogen, the method comprising: (a) providing a composition comprising LAL, wherein the LAL comprises coagulogen; (b) adjusting the buffer; and (c) subjecting the composition of (b) to tangential flow filtration using a 20 kDa to 50 kDa filter and collecting the retentate, thereby isolating LAL substantially free of coagulogen.

The membranes use in the method disclosed herein can include, but are not limited to modified Polyethersulfone (mPES), Polysulfone (PS) and Polyethersulphone (PES). In some embodiments, the method of making LAL substantially free of coagulogen is performed using TFF using a modified polyethersulfone (mPES) membrane filter. The rate of flow of the LAL across the membranes can be adjusted to optimize removal of the coagulogen from the LAL. In some embodiments, the TFF is performed at a flow rate of 200 ml/min to 800 ml/min, 300 ml/min to 600 ml/min, or 350 ml/min to 500 ml/min.

EXAMPLES

Example 1

Purification of LAL Using Tangential Flow Filtration

Limulus amebocyte lysate (LAL) extracted from blood cells (amoebocytes) of horseshoe crab was obtained from Lonza (Basel, Switzerland). The LAL was subjected to hollow fiber modified polyethersulfone (mPES) membrane filters (SpectrumLabs) for tangential flow filtration (TFF) to remove the coagulogen. The TFF system was set up using a 30 kDa MWCO mPES filter, Cole Parmer Masterflex Pump Tubing and the appropriate pump and backpressure valve. The system was flushed with LAL reagent water (LRW), then depyrogenated using 1N NaOH for 1 hr at room temperature. LRW was used to rinse the system after depyrogenation then the system was equilibrated using TFF buffer.

The LAL was diluted at a ratio of 1:10 to 1:8 with TFF buffer (50 mM Tris with 77 mM NaCl at pH 7.4-7.5 at room temperature) before being fed into the filter at a flow rate of 430 ml/min while maintaining a transmembrane pressure (TMP) of 5-8 psi until 90% of the total volume was collected in the permeate. The retentate was then further diluted at a ratio of 1:10 to 1:8 with TFF buffer and then fed into the filter. Retentate dilution was repeated and the LAL was processed until the volume of the retentate was the same as the initial volume of LAL. Coagulogen was collected in the permeate while the remaining proteins were retained in the retentate. SDS-PAGE and Western blot analysis of the permeate and retentate showed that coagulogen was substantially reduced in the retentate.

During the TFF optimization process, a buffer comprising 50 mM MES with 77 mM NaCl at pH 6.2, was also used. However, the highest percentage of total protein removed from the LAL was seen with the Tris buffer.

All buffers were tested for endotoxin using standard KQCL kits from Lonza before being used for TFF.

Example 2

Quantification of Coagulogen

Figure 7A:
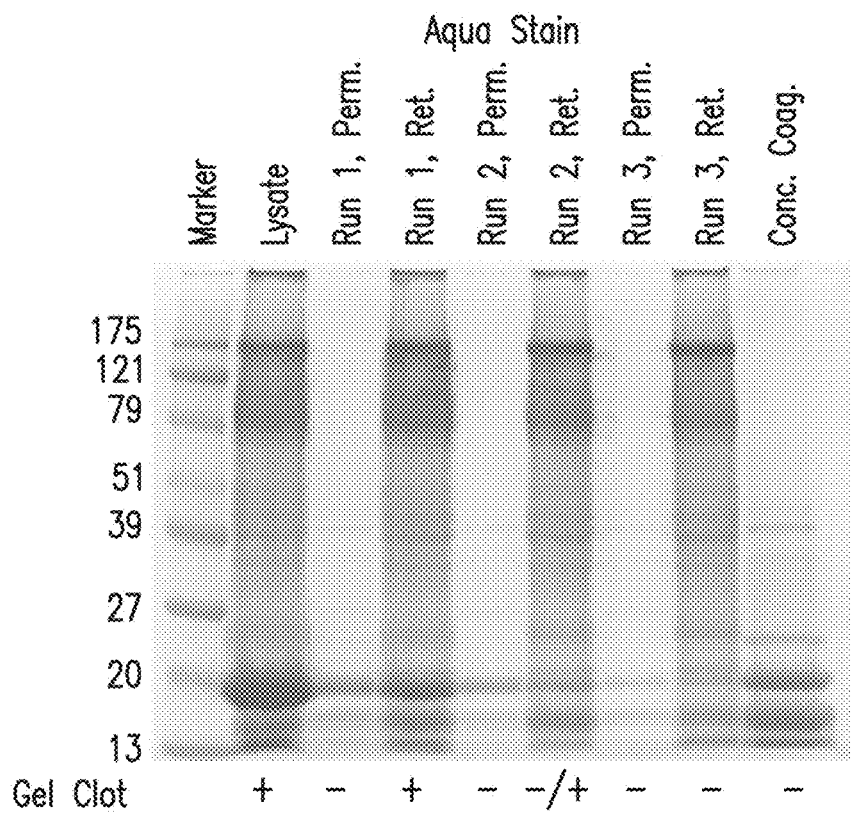
FIG. 7A: SDS-PAGE gel analysis of LAL samples subjected to tangential flow filtration (TFF) (30 kDa), and the TFF products run under reducing conditions for three runs. After the third run, no gel clotting is observed. Gel clot data represented as "+" for solid gel clot, "−" for no gel clot and "−/+" for soft gel clot.

Semi-quantitative evaluation of the remaining coagulogen in the LAL was conducted by performing SD S-PAGE/protein gel stain on the LAL retentate and comparing the band density of the 20 kD coagulogen band in the original LAL to the coagulogen band, if any, in the TFF retentate. See, e.g., FIG. 7A.

Figure 7B:
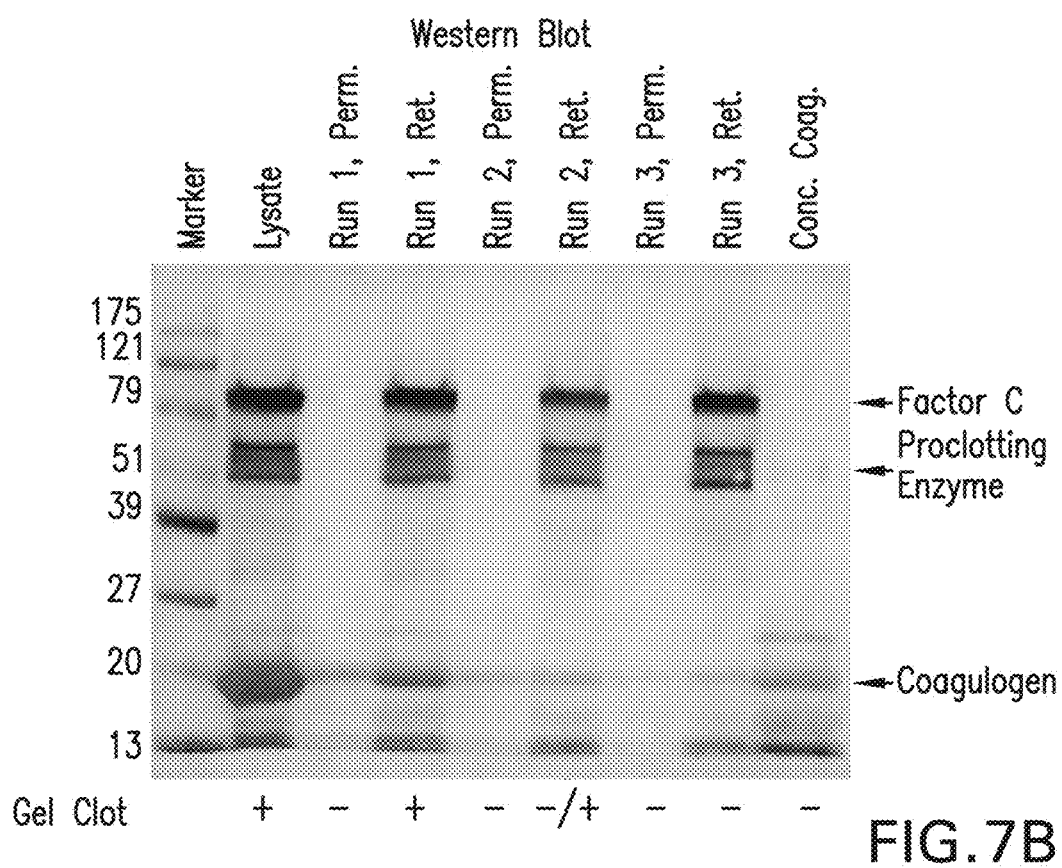
FIG. 7B: Western blot analysis of tangential flow filtration (30 kDa) products run under reducing conditions for three runs. Antibody dilutions were as follows: α-coagulogen 1:1,000, α-proclotting enzyme 1:10,000, α-sushi 3 1:100.

Additionally, an α-coagulogen antibody was used to perform a Western blot then compare the band density of the 20 kD coagulogen bands. See, e.g., FIG. 7B.

Figure 9:
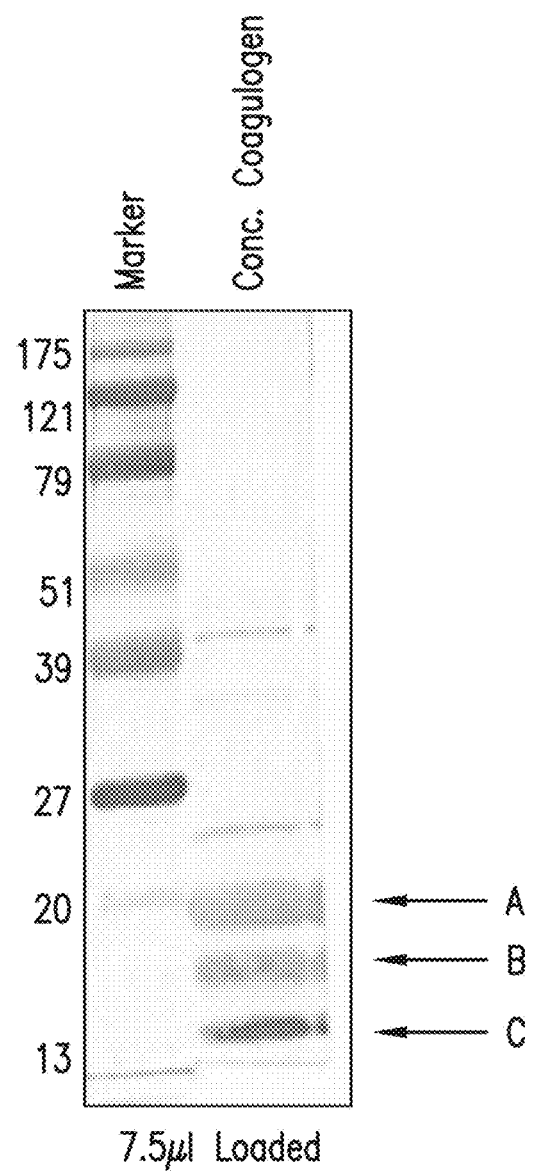
FIG. 9: SDS-PAGE of coagulogen. When run33 under reducing conditions, three bands of coagulogen are present. Protein sequencing confirmed that the three bands are coagulogen fragments. A=coagulogen1:pos 21 GDPNVPTCLC (SEQ ID NO: 2); B=coagulogen2: pos 39 KVIVSQEKTD (SEQ ID NO: 3); C=coagulogen3: pos 67 GFSIFGGHPA (SEQ ID NO: 4).

The identity of coagulogen was confirmed by running the LAL permeate (containing the coagulogen) under reducing conditions on an SDS-PAGE gel, and then sequencing the three bands. See FIG. 9. Each of the three bands was confirmed as a coagulogen fragment by protein sequencing.

Both quantitative methods confirm the present invention removed a substantial percentage of coagulogen from the LAL.

Figure 8A:
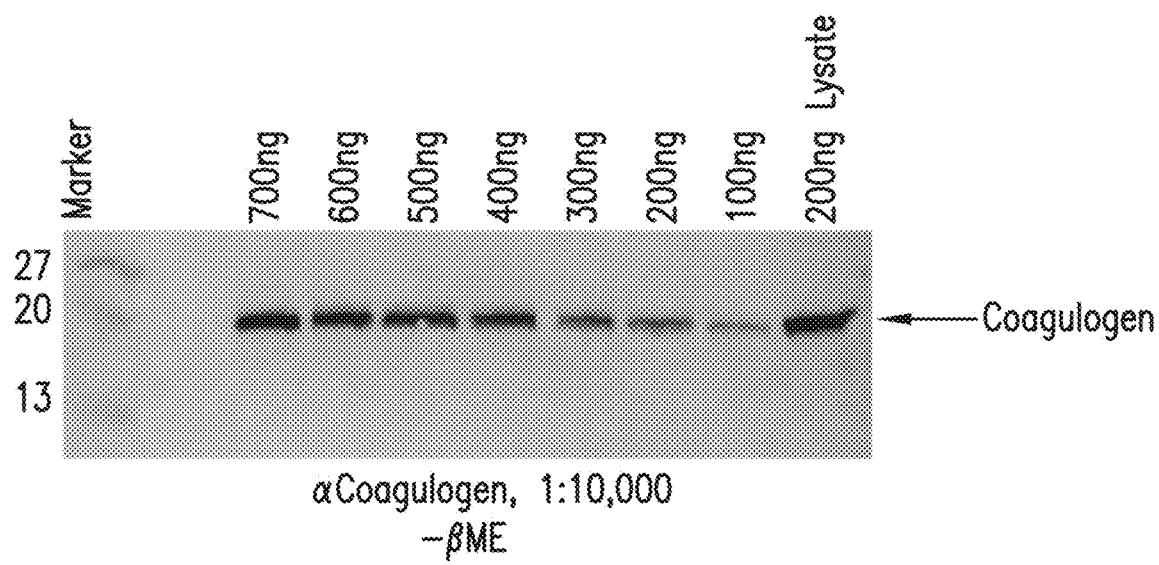
FIG. 8A: Quantification of coagulogen using Western blot analysis using α-coagulogen.
Figure 8B:
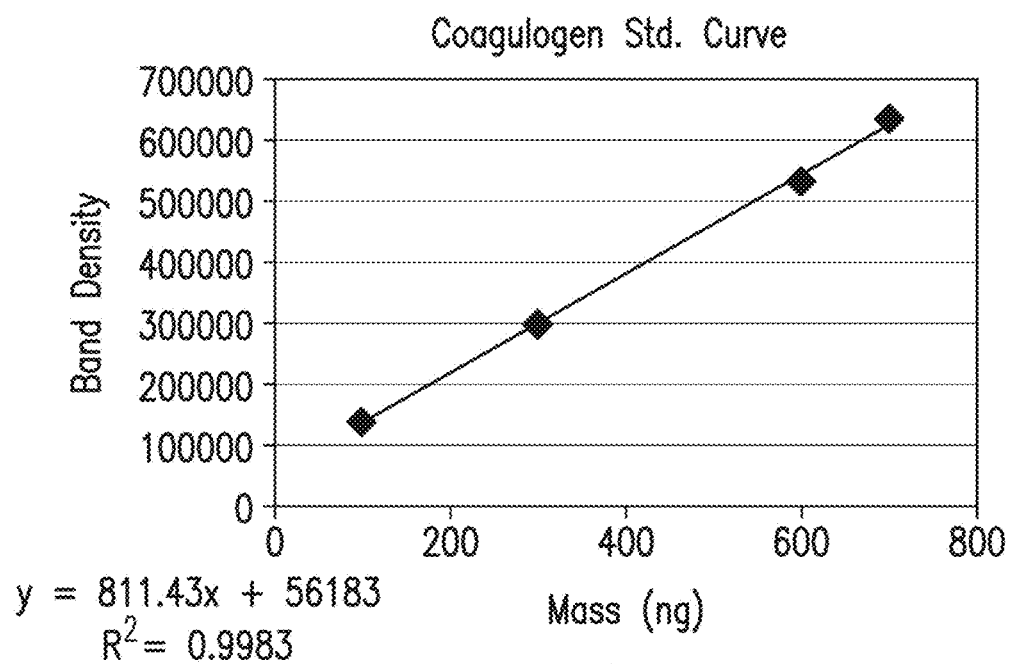
FIG. 8B: The data of FIG. 8A plotted to a standard curve. The data suggests about 33% of total LAL protein is coagulogen.

The amount of coagulogen in LAL was determined using Western blot analysis. FIG. 8A. The results of the Western blot analysis were fit to a standard curve. FIG. 8B. The results indicated that about 662 ng/2000 ng, or about 33% of the total protein in LAL is coagulogen.

Example 3

Stability of LAL Substantially Free of Coagulogen

The stability of the LAL substantially free of coagulogen was investigated. LAL substantially free of coagulogen samples were stored for 1, 2, 3, 4, 5, 6, 7, 8, 9 and 10 weeks. At the end of the indicated time period, the LAL substantially free of coagulogen sample is mixed with the LAL chromogenic reagent in a 96-well plate and placed in an incubating plate reader that measures absorbance at 405 nm. The reaction was automatically monitored over time the appearance of a yellow color.

Figure 10A:
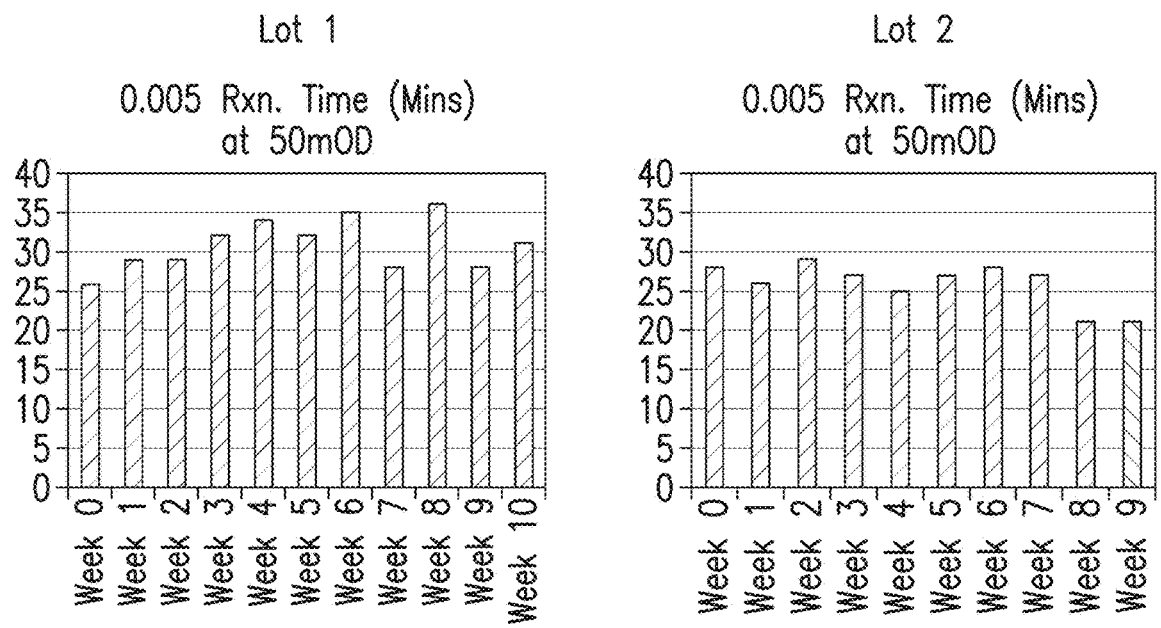
FIG. 10A and FIG. 10B: Stability of two separate lots of L-co was determined over ten weeks at 50 mOD. The data suggests that the L-co was stable over the 10 week period.
Figure 10B:
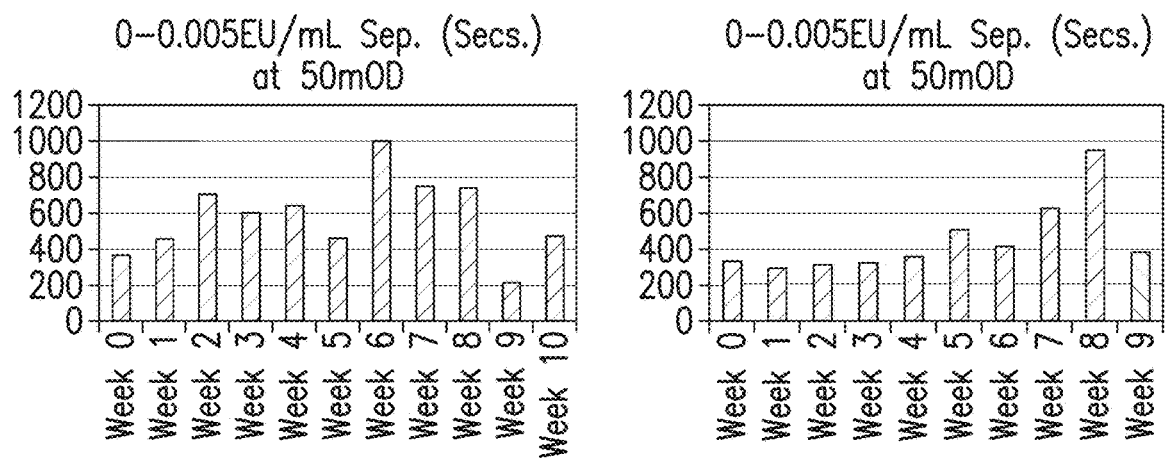
Figures 11A, 11B:
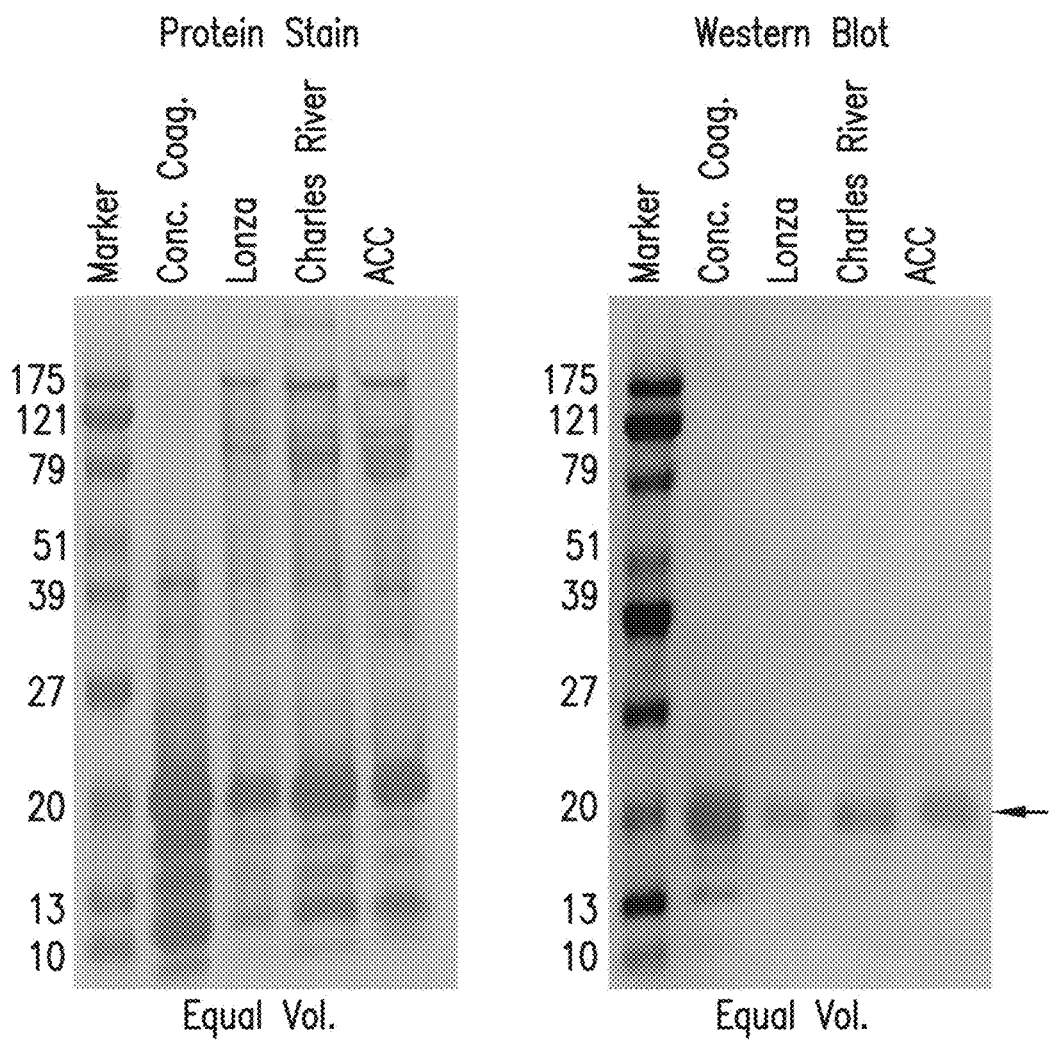
FIG. 11A and FIG. 11B: The presence of coagulogen in commercially available LAL from Lonza, Charles River Laboratories International, and Associates of Cape Cod, Inc. (ACC) was tested using SDS-PAGE with a protein stain and with Western Blot analysis. This confirmed that LAL from all three suppliers contained coagulogen.

In the presence of endotoxin, the lysate will cleave the chromogenic substrate, causing the solution to become yellow. The time required for the change is inversely proportional to the amount of endotoxin present. Time required to reach 50 mOD for each of the samples is found in FIG. 10. The data suggests LAL substantially free of coagulogen is stable for at least 10 weeks.

Example 4

Coagulogen Removal Improves Separation

An investigation of the effect that removing coagulogen from LAL had on the separation at multiple onset mOD was conducted. A comparison of regular LAL versus LAL substantially free of coagulogen showed an increase in separation at each onset mOD, when LAL substantially free of coagulogen was used. By using LAL substantially free of coagulogen to increase separation, the target sensitivity of the assay can be achieved in less time at lower onset mOD settings. A target sensitivity of 0.005 EU/ml can be achieved in 26 minutes with separation of 368 seconds when LAL substantially free of coagulogen is used to prepare the formulation. When regular LAL is used, a sensitivity of 0.005 EU/ml is achieved in 32 minutes but with only 67 seconds of separation at 50 mOD.

The data suggests that coagulogen removal from LAL improves separation.

Example 5

Chromogenic Detection of LAL and LAL Substantially Free of Coagulogen Formulations Samples of both LAL and LAL substantially free of coagulogen were tested at 20%, 30%, 40% and 50% concentrations in the LAL preparation against a standard of 0.005 EU/ml, 0.05 EU/ml, 0.5 EU/ml, 5 EU/ml and 50 EU/ml. Additionally, various concentrations of zwittergent were also tested. FIG. 3 and FIG. 4. The data suggests that increasing the concentration of LAL substantially free of coagulogen and zwittergent increased the speed of reaction for each standard for both the LAL and LAL substantially free of coagulogen formulations. However, separation is lost between the blank and lowest standard (0.005 EU/ml) as the speed of the reaction increases with the LAL formulation, while a separation of at least 200 seconds is maintained for all LAL substantially free of coagulogen formulations. LAL substantially free of coagulogen formulated with increased zwittergent achieved sensitivity of 0.001 EU/ml with acceptable separation. (Data not shown).

Example 6

Ratio of LAL Substantially Free of Coagulogen and Chromogenic Substrate

The optimal ratio of LAL substantially free of coagulogen and chromogenic substrate was investigated at 200 mOD and 50 mOD. FIG. 5A and FIG. 5B. The data indicates that a ratio of 70% LAL preparation and 30% chromogenic substrate resulted in the fastest reaction times. This observation was confirmed when looking at three different lots of LAL substantially free of coagulogen. FIG. 6A.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

---

---

What is claimed is:

1. A method of making limulus amebocyte lysate (LAL) substantially free of coagulogen, wherein the LAL substantially free of coagulogen comprises less than 5% (wt/wt) of coagulogen relative to total protein in the LAL as measured by SDS-PAGE with protein stain, comprising:
   subjecting a composition comprising LAL, wherein the LAL comprises coagulogen, to tangential flow filtration (TFF) using a 20 kDa to 50 kDa TFF filter, wherein the TFF produces a retentate and a filtrate; and
   collecting the retentate, thereby obtaining the LAL substantially free of coagulogen.

2. The method of claim 1, wherein the TFF is performed at a flow rate of 300 ml/min to 600 ml/min.

3. The method of claim 2, wherein the TFF is performed at a flow rate of 350 ml/min to 500 ml/min.

4. The method of claim 1, wherein the composition comprising LAL is in a buffer.

5. The method of claim 4, wherein the buffer is a Tris buffer or IVIES buffer.

6. The method of claim 4, wherein the buffer has a pH of about 6.0 to about 9.0.

7. The method of claim 6, wherein the buffer has a pH of about 7.0 to about 8.0.

8. The method of claim 1, wherein the TFF filter comprises a membrane selected from modified polyethersulfone (mPES), polysulfone (PS) and polyethersulphone (PES).

9. The method of claim 8, wherein the TFF filter comprises a mPES membrane filter.

10. The method of claim 1, wherein the LAL substantially free of coagulogen comprises less than 1% (wt/wt) of coagulogen relative to total protein in the LAL as measured by SDS-PAGE with protein stain.

11. The method of claim 10, wherein the LAL substantially free of coagulogen comprises less than 0.5% (wt/wt) of coagulogen relative to total protein in the LAL as measured by SDS-PAGE with protein stain.

\* \* \* \* \*

UNITED STATES PATENT AND TRADEMARK OFFICE
CERTIFICATE OF CORRECTION

| | |
|---|---|
| PATENT NO. | : 11,906,521 B2 |
| APPLICATION NO. | : 17/482918 |
| DATED | : February 20, 2024 |
| INVENTOR(S) | : Candice Stumbaugh, David S. Herbst and Kenneth E. Nichols, Jr. |

It is certified that error appears in the above-identified patent and that said Letters Patent is hereby corrected as shown below:

In the Claims

Column 16, Line 54 (Claim 5):
"IVIES" should be replaced with --MES--.

Signed and Sealed this
Seventh Day of May, 2024

Katherine Kelly Vidal
Director of the United States Patent and Trademark Office

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term pNA

<400> SEQUENCE: 1

Ile Glu Ala Arg
1

<210> SEQ ID NO 2
<211> LENGTH: 10
<212> TYPE: PRT
<213> ORGANISM: Limulus polyphemus

<400> SEQUENCE: 2

Gly Asp Pro Asn Val Pro Thr Cys Leu Cys
1               5                   10

<210> SEQ ID NO 3
<211> LENGTH: 10
<212> TYPE: PRT
<213> ORGANISM: Limulus polyphemus

<400> SEQUENCE: 3

Lys Val Ile Val Ser Gln Glu Lys Thr Asp
1               5                   10

<210> SEQ ID NO 4
<211> LENGTH: 10
<212> TYPE: PRT
<213> ORGANISM: Limulus polyphemus

<400> SEQUENCE: 4

Gly Phe Ser Ile Phe Gly Gly His Pro Ala
1               5                   10